US012600855B2

(12) United States Patent
    Itakura et al.

(10) Patent No.: US 12,600,855 B2
(45) Date of Patent: Apr. 14, 2026

(54) BIODEGRADATION ACCELERATOR FOR BIODEGRADABLE RESIN

(71) Applicant: Daicel Corporation, Osaka (JP)

(72) Inventors: Masahiko Itakura, Tokyo (JP);
    Takayuki Ogihara, Tokyo (JP);
    Shinichiro Imanishi, Tokyo (JP);
    Shohei Yasuoka, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 495 days.

(21) Appl. No.: 18/029,126

(22) PCT Filed: Oct. 20, 2021

(86) PCT No.: PCT/JP2021/038788
    § 371 (c)(1),
    (2) Date: Mar. 29, 2023

(87) PCT Pub. No.: WO2022/085725
    PCT Pub. Date: Apr. 28, 2022

(65) Prior Publication Data
    US 2023/0365805 A1     Nov. 16, 2023

(30) Foreign Application Priority Data

Oct. 20, 2020    (JP) ................................. 2020-175857
    Jun. 11, 2021    (JP) ................................. 2021-097762
    Aug. 12, 2021    (JP) ................................. 2021-131542

(51) Int. Cl.
    *C08L 67/04*        (2006.01)
    *A61L 31/14*        (2006.01)
    (Continued)

(52) U.S. Cl.
    CPC ............. *C08L 67/04* (2013.01); *A61L 31/148* (2013.01); *A61L 31/16* (2013.01);
    (Continued)

(58) Field of Classification Search
    CPC combination set(s) only.
    See application file for complete search history.

(56) References Cited

U.S. PATENT DOCUMENTS 3,709,720 A * 1/1973 Kindl et al. .......... B29C 48/151
                                                    264/188
3,864,499 A * 2/1975 Turbak ............... A22C 13/0013
                                                    426/138
(Continued)

FOREIGN PATENT DOCUMENTS

EP        0654492 A2    5/1995
JP        4357859 B2    11/2009
(Continued)

OTHER PUBLICATIONS

Cellophane (CE), Netherlands Institute for Conservation and Arts and Sciences, pp. 1-3, 2025 (Year: 2025).*
(Continued)

*Primary Examiner* — Peter A Salamon
(74) *Attorney, Agent, or Firm* — XSENSUS LLP

(57) ABSTRACT

[Problem] To provide a biodegradation accelerator for a biodegradable resin to accelerate biodegradation of the biodegradable resin.
[Solution] A biodegradation accelerator for a biodegradable resin, the biodegradation accelerator containing a regenerated cellulose, in which the regenerated cellulose is selected from the group consisting of fibers, molded products including films, powders, cotton-like objects, and intermediate molded bodies, and a biodegradation speed for a biodegradable resin is accelerated compared to a case where the biodegradation accelerator for a biodegradable resin is not used.

11 Claims, 1 Drawing Sheet

(51) Int. Cl.

| | | |
|---|---|---|
| *A61L 31/16* | (2006.01) | |
| *B29B 17/04* | (2006.01) | |
| *C08J 11/10* | (2006.01) | |
| *C08L 67/02* | (2006.01) | |

(52) U.S. Cl.
   CPC ......... *B29B 17/0412* (2013.01); *C08J 11/105* (2013.01); *C08L 67/02* (2013.01); *C08L 2201/06* (2013.01); *C08L 2205/16* (2013.01)

(56) References Cited

U.S. PATENT DOCUMENTS

| | | | | |
|---|---|---|---|---|
| 5,434,004 | A * | 7/1995 | Ajioka | B32B 27/06 |
| | | | | 428/411.1 |
| 5,714,230 | A * | 2/1998 | Kameoka | C08L 67/02 |
| | | | | 428/221 |
| 9,119,419 | B2 * | 9/2015 | Sebastian | A24D 3/068 |
| 2003/0077961 | A1 * | 4/2003 | Cates | D06P 5/30 |
| | | | | 442/152 |
| 2005/0235556 | A1 * | 10/2005 | Girard | C09K 17/52 |
| | | | | 47/9 |
| 2005/0246949 | A1 * | 11/2005 | Girard | C09K 17/52 |
| | | | | 47/9 |
| 2005/0246950 | A1 * | 11/2005 | Girard | A01G 13/35 |
| | | | | 47/9 |
| 2005/0282456 | A1 * | 12/2005 | Zhao | D04H 1/587 |
| | | | | 604/366 |
| 2014/0096783 | A1 * | 4/2014 | Sebastian | A24D 3/068 |
| | | | | 264/103 |
| 2015/0189913 | A1 * | 7/2015 | Binassi | A24D 3/04 |
| | | | | 131/331 |
| 2017/0072596 | A1 * | 3/2017 | Oguni | C08L 51/06 |

FOREIGN PATENT DOCUMENTS

| | | |
|---|---|---|
| JP | 2010-241075 A | 10/2010 |
| JP | 2016-191021 A | 11/2016 |
| JP | 2016-191183 A | 11/2016 |
| JP | 6551726 B2 | 7/2019 |

OTHER PUBLICATIONS

What are the Properties of Polylactic Acid, PLAMFG, pp. 1-10, 2023 (Year: 2023).*

International Preliminary Report On Patentability (Chapter I) and English translation of Written Opinion mailed on May 4, 2023, in corresponding PCT/JP2021/038788, 6 pages.

* cited by examiner

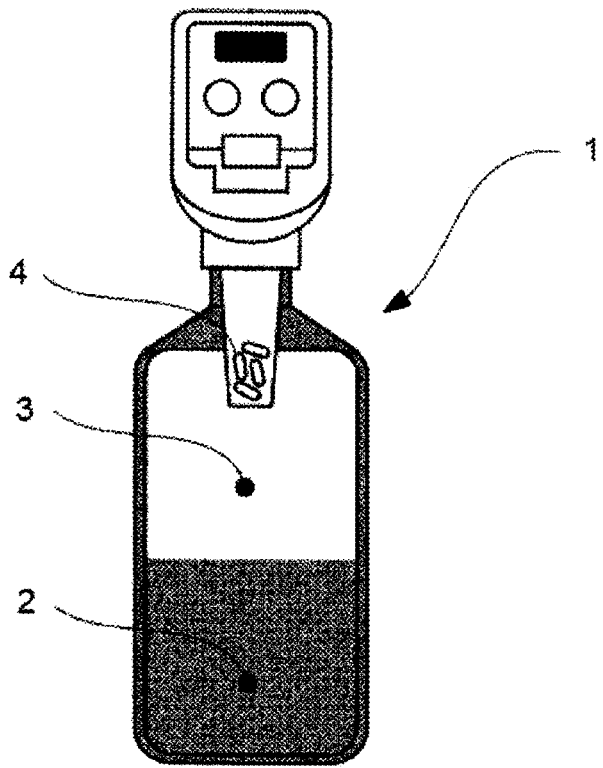

BIODEGRADATION ACCELERATOR FOR BIODEGRADABLE RESIN

CROSS-REFERENCE TO RELATED APPLICATIONS

The present application is based on PCT filing PCT/JP2021/038788, filed Oct. 20, 2021, which claims priority to Japanese Patent Applications No. 2020-175857, filed on Oct. 20, 2020, JP 2021-097762 filed on Jun. 11, 2021 and JP 2021-131542 filed on Aug. 12, 2021, the entire contents of each are incorporated herein by reference.

TECHNICAL FIELD

The present disclosure relates to, in its representative aspect, a biodegradation accelerator for a biodegradable resin. The present disclosure also relates to, in its other representative aspects, a biodegradation acceleration method for a biodegradable resin, a biodegradable resin composition containing the biodegradation accelerator for a biodegradable resin, a biodegradable resin molded product containing the biodegradable resin composition, and a treatment method for a biodegradable resin molded product to be disposed by using the biodegradation accelerator for a biodegradable resin.

BACKGROUND ART

The pollution of the environment such as soil, rivers, and ocean due to wastes originated from disposed plastic products has been problematic. To solve the problem, separate collection, reuse, and appropriate incineration treatment of wastes originated from plastic products are important; however, this approach alone would not solve the problem sufficiently when the problem is considered on a global scale.

Thus, there is a demand for development and use of a biodegradable resin that undergoes biological decomposition in the natural environment as a means of solving the problem, and in particular, development and use of a biodegradable resin that undergoes biological decomposition in the sea.

JP 2010-241075 A describes an invention of a method of producing a biodegradable resin molded product, in which the method produces a molded product by heating and melt-kneading a biodegradable resin composition containing an aliphatic polyester-based polymer. Specifically, production of 3-hydroxybutyrate-co-3-hydroxyhexanoate (PHBH) as the aliphatic polyester-based polymer is described (Claims and Examples).

The website (Oct. 31, 2019) of the applicant of JP 2010-241075 A describes that the PHBH has marine biodegradability and is produced on a commercial basis as straws.

JP 2016-191021 A describes an invention of a base material for composite molding, in which the base material includes regenerated cellulose fibers and a thermoplastic resin containing polycarbonate and polylactic acid. However, due to high content proportion of the polycarbonate, the base material for composite molding itself does not have biodegradability.

JP 3478299 B described an invention of a degradable composite material containing a thermoplastic polymer composition containing an aliphatic polyester, and a cellulose selected from wood pulps, fibers made of wood pulps, nonwoven fabrics, regenerated celluloses other than regenerated cellulose films, cellulose esters, or cellulose ethers.

The degradable composite material is obtained by 1) a method in which the cellulose is subjected to impregnated with or coating of the aliphatic polyester or a solution thereof, 2) a method in which the aliphatic polyester in a fiber form or pulp form and fibers or pulps of the cellulose are mixed and pressure-bonded by heat, and 3) a method of bonding films of the cellulose and of the aliphatic polyester by heat or an adhesive.

JP 4357859 B describes an invention of a fiber composite resin product including a base material layer of a composite material of first fibers and a first thermoplastic resin, and a surface layer of a second composite material of second fibers and a second thermoplastic resin, the surface layer being on the base material layer. The first fibers are selected from the group consisting of glass, kenaf, hemp, bamboo, wood pulps, coconut shells, and rush, and the second fibers each have a fiber diameter of 15 μm to 50 μm, and the second fibers are selected from the group consisting of rayon, cotton, fleece, straw, polyesters, silk, nylon, and wool.

JP 6551726 B describes an invention of a fiber sheet for composite molding, the fiber sheet containing regenerated cellulose fibers and thermoplastic resin fibers, a mixed ratio (mass ratio) of the regenerated cellulose fibers to the thermoplastic resin fibers being from 20:80 to 60:40, a fineness of the regenerated cellulose fibers being 0.1 dtex or more and less than 1.0 dtex and a fiber length being 1.0 mm or more. In JP 6551726 B, the thermoplastic resin fibers are selected from the group consisting of polycarbonate fibers, polylactic acid fibers, polypropylene fibers, and polymethylpentene fibers.

SUMMARY OF INVENTION

In the present disclosure, in its representative aspect, an object is to provide a biodegradation accelerator for a biodegradable resin, the biodegradation accelerator being capable of accelerating biodegradation of a biodegradable resin in the natural environment. In the present disclosure, in its other representative aspects, another object is to provide a biodegradation acceleration method for a biodegradable resin using the biodegradation accelerator, a biodegradable resin composition containing the biodegradation accelerator for a biodegradable resin, a biodegradable resin molded product containing the biodegradable resin composition, and a treatment method for a biodegradable resin molded product by using the biodegradation accelerator for a biodegradable resin.

In its representative aspect, the present disclosure provides a biodegradation accelerator for a biodegradable resin, the biodegradation accelerator containing a regenerated cellulose, in which the regenerated cellulose is selected from the group consisting of fibers, molded products including films, powders, cotton-like objects, and intermediate molded bodies, and a biodegradation speed for a biodegradable resin is accelerated compared to a case where the biodegradation accelerator for a biodegradable resin is not used.

In its another representative aspect, the present disclosure provides a biodegradation acceleration method for a biodegradable resin, the method using the biodegradation accelerator. In its another representative aspect, the present disclosure provides a biodegradable resin composition containing the biodegradation accelerator for a biodegradable resin. In its another representative aspect, the present disclosure provides a biodegradable resin molded product made of the biodegradable resin composition. In its another representative aspect, the present disclosure provides a method for treating a biodegradable resin molded product using the biodegradation accelerator for a biodegradable resin.

The biodegradation accelerator for a biodegradable resin according to an example of the present disclosure has acceleration action for biodegradability of a biodegradable resin. The same acceleration action can be also obtained by the biodegradation acceleration method for a biodegradable resin produced by using the biodegradation accelerator, the biodegradable resin composition containing the biodegradation accelerator for a biodegradable resin, and the biodegradable resin molded product containing the biodegradable resin composition.

BRIEF DESCRIPTION OF DRAWINGS

FIG. 1 is a front view of a testing equipment to perform a sea water biodegradability test used in Examples of the present disclosure. However, a part thereof is illustrated as a cross-sectional view to illustrate the internal structure.

DESCRIPTION OF EMBODIMENTS

Biodegradation Accelerator for Biodegradable Resin

According to one example, the biodegradation accelerator for a biodegradable resin may contain a regenerated cellulose, and the biodegradation speed of the biodegradable resin is accelerated compared to a case where the biodegradation accelerator for a biodegradable resin is not used.

The biodegradation accelerator for a biodegradable resin may contain only a regenerated cellulose or may contain a combination of a regenerated cellulose and another component.

The regenerated cellulose may be obtained by melting cellulose or a derivative thereof into a liquid form and forming the melt into a desired shape. The regenerated cellulose is vastly different from a natural cellulose in that, depending on the intended features such as biodegradation speed or the like, its size or shape can be appropriately selected for the regenerated cellulose.

The regenerated cellulose may be selected from the group consisting of fibers, molded products including films, powders, cotton-like objects, and intermediate molded bodies.

The regenerated cellulose may preferably have a degree of crystallinity of 80% or less, or a degree of crystallinity of 60% or less. Alternatively, an amorphous regenerated cellulose having a degree of crystallinity of 10% or less can be used.

As the regenerated cellulose fibers, known fibers such as Viscose rayon, Cupra (cuprammonium rayon), Fortisan, Lyocell (solvent spinning cellulose fibers), BIOMID (solvent spinning cellulose fibers), and Bocel can be used.

As the regenerated cellulose film, Cellophane or the like can be used. As the regenerated cellulose particles, Viscopearl (Rengo Co., Ltd.), NanoAct (Asahi Kasei Corporation), or the like can be used, and crushed materials of regenerated cellulose fibers or films can be also used.

For Viscose rayon, Cellophane, and Viscopearl, there is a problem of the use of carbon disulfide, which is highly toxic and flammable, during production. As the production method of the regenerated cellulose, a method in which cellulose is directly dissolved in a solvent (solvating media) and then subjected to spinning, film formation, powderization, or flocculation is preferred.

The regenerated cellulose used in the present disclosure can be obtained by dissolving cellulose in solvents 1 to 4 described below, and pouring the solution into a poor solvent. The solvents 1 to 4 may be used alone or in combination.

1. Ionic Liquid

The ionic liquid refers to a liquid that is liquid at 150° C. or lower and contains an organic ion.

An anion moiety of the ionic liquid in the present disclosure is not particularly limited, and those typically used for an anion moiety of an ionic liquid can be used.

Preferred examples of the anion moiety of the ionic liquid in the present disclosure include halogen anions, a carboxylate anion, a phosphoric acid anion, and a cyanide anion.

A cation moiety of the ionic liquid in the present disclosure is not particularly limited, and those typically used for a cation moiety of an ionic liquid can be used.

Preferred examples of the cation moiety of the ionic liquid in the present disclosure include a phosphonium cation and nitrogen-containing aromatic cations.

Examples of the nitrogen-containing aromatic cation include a pyridinium cation, a pyridazinium cation, a pyrimidinium cation, a pyrazinium cation, an imidazolium cation, a pyrazonium cation, an oxazolium cation, a 1,2,3-triazolium cation, a 1,2,4-triazolium cation, a thiazolium cation, a piperidinium cation, and a pyrrolidinium cation.

Specific examples of the ionic liquid include 1-ethyl-3-methylimidazolium acetate, 1-butyl-3-methyl imidazolium acetate, 1-butyl-3-methylimidazolium chloride, 1-butyl-3-methylimidazolium phosphinate, 1-butyl-3-methylimidazolium methylphosphonate, 1-ethyl-3-methylimidazolium methylphosphonate, and 1-ethyl-3-methylimidazolium chloride.

2. Alkali Metal Hydroxide Aqueous Solution

An aqueous solution of an alkali metal hydroxide, such as sodium hydroxide or potassium hydroxide, can be used. From 35 to 60 mass % sodium hydroxide aqueous solution is preferable. As a dissolution aid, urea or thiourea may be contained.

3. Onium Compound Aqueous Solution

An onium compound aqueous solution can be used.

The onium compound includes quaternary phosphonium compounds and quaternary ammonium compounds.

As the quaternary phosphonium compound, a quaternary phosphonium hydroxide is preferred. Typical examples of the quaternary phosphonium hydroxide include tetraalkylphosphonium hydroxides containing an alkyl group having from 2 to 8 carbons such as tetraethylphosphonium hydroxide, tetrapropylphosphonium hydroxide, tetrabutylphosphonium hydroxide, and tetrahexylphosphonium hydroxide.

As the quaternary ammonium compound, a quaternary ammonium hydroxide is preferred. Typical examples of the quaternary ammonium hydroxide include tetraalkylammoniumhydroxides containing an alkyl group having from 2 to 8 carbons such as tetraethylammonium hydroxide, tetrapropylammonium hydroxide, tetrabutylammonium hydroxide, and tetrahexylammonium hydroxide.

The onium compound may be a salt of an onium cation and an anion such as halide anions, a tetrafluoroborate anion, a tetrafluorophosphate anion, or a trifluoromethanesulfonate anion, and is preferably onium hydroxide.

4. Other Solvent

Examples of other solvent include amide-based solvents such as N,N-dimethylacetamide, N,N-dimethylformamide, and N-methylpyrrolidone; sulfoxide-based solvents such as dimethyl sulfoxide and hexamethylene sulfoxide; nitrilebased solvents such as acetonitrile and propionitrile; cyclic ether-based solvents such as N-methyl-morpholine-N-oxide aqueous solutions, 1,3-dioxolane, and tetrahydrofuran; amine-based solvents such as pyridine; N-methylmorpholine-N-oxide aqueous solutions; and water.

These solvents may be allowed to coexist with a dissolution aid. Examples of the dissolution aid include, but not limited to, lithium chloride and lithium bromide.

The fineness, fiber length, and the like of the regenerated cellulose fibers are not particularly limited and, for example, a known numerical ranges described in JP 2016-191021 A can be employed.

Examples of the regenerated cellulose fibers include powder of regenerated cellulose fibers, a shredded material or beaten material of the regenerated cellulose fibers, a woven fabric made of the regenerated cellulose fibers or a cut material or beaten material thereof, a nonwoven fabric made of the regenerated cellulose fibers or a cut material or beaten material thereof, a knitted material of the regenerated cellulose fibers or a cut material or beaten material thereof, yarn made of the regenerated cellulose fibers or a cut material or beaten material thereof, or a string made of the regenerated cellulose fibers or a cut material or beaten material thereof.

(i) As an example of the regenerated cellulose fibers, a material obtained by kneading a cut material (e.g., approximately 3 mm) of regenerated cellulose fibers and a biodegradable resin using an extruder, then extruding the kneaded material in a strand form, and cooling and cutting the extruded material by a pelletizer can be used.

(ii) Pellets obtained by, without cutting the regenerated cellulose fibers, taking out a continuous fiber from a creel, coating the fiber bundle with a resin using an extruder equipped with a coating die, and then cutting the fiber bundle covered with the resin by a pelletizer can be also used.

(iii) Alternatively, pellets obtained as described above are supplied into an extruder and the fibers are dispersed more uniformly. The pellets thus obtained can be used.

(iv) Furthermore, as another example of the regenerated cellulose fibers, the regenerated cellulose fiber bundle obtained by the following procedure may be used: long regenerated cellulose fibers are arranged in a length direction and bundled; to this bundle, a molten biodegradable resin is deposited or impregnated to form a combined material; the combined material is cut to the length of 3 to 30 mm; and thus the regenerated cellulose fiber bundle is obtained. This regenerated cellulose fiber bundle can be produced in the same manner as in, for example, Production Example 1 of JP 6711876 B and Production Example 1 of JP 6453575 B.

By selecting any one of the mixing methods (i) to (iv), the fiber length of the fibers to be dispersed in the biodegradable resin can be controlled. According to some examples, the fiber lengths in the resulting composition are in the order of, long to short, (iv)>(ii)>(i) and (iii).

By further adjusting the processing conditions, further control can be performed. For example, in (i), by making the first cut length of the regenerated cellulose fibers short, the length of fibers in the resulting composition can be made short.

As the molded product including film, a film or a film processed product can be used.

The intermediate molded body is a material in middle of the process of forming fibers, films, or the like from a cellulose or derivatives thereof, and examples of the intermediate molded body include those in a solution form.

According to some examples, the biodegradation accelerator for a biodegradable resin can further contain a biodegradable resin in addition to the regenerated cellulose.

Examples of the biodegradable resin include one or more selected from the group consisting of cellulose ester, starch polyester, polylactic acid (PLA), poly (3-hydroxybutyrate-co-3-hydroxyhexanoate) (PHBH), polylactic acid/polycaprolactone copolymers, polyglycolic acid (PGA), polylactic acid/polyether copolymers, butanediol/long-chain dicarboxylic acid copolymers, polybutylene adipate/terephthalate (PBAT), polytetramethylene adipate-co-terephthalate, polyethylene terephthalate succinate (PETS), polybutylene succinate (PBS), polybutylene succinate adipate (PBSA), and polyvinyl alcohol (PVA).

When the biodegradable resin is a cellulose ester, examples of the biodegradable resin include those selected from the group consisting of cellulose acetate, cellulose propionate, cellulose butyrate, cellulose acetate propionate, cellulose acetate butyrate, polycaprolactone grafted cellulose acetate, acetyl methyl cellulose, acetyl ethyl cellulose, acetyl propyl cellulose, acetyl hydroxyethyl cellulose, and acetyl hydroxypropyl cellulose.

The biodegradable resin may be cellulose acetate in a preferred aspect of the present disclosure.

Furthermore, from the perspective of acting as a biodegradation accelerator for a biodegradable resin, the cellulose acetate preferably has a degree of substitution of 2.8 or less, more preferably has a degree of substitution of 2.5 or less, and even more preferably has a degree of substitution of 2.1 or less.

Even in a case where the biodegradation accelerator for a biodegradable resin contains the regenerated cellulose fibers and the biodegradable resin, the biodegradation accelerator preferably contains no non-biodegradable resin; however, the biodegradation accelerator may contain a small amount of non-biodegradable resin for the reason that, for example, the production facility of the biodegradation accelerator can be shared with a product using a non-biodegradable resin.

In a case where the biodegradation accelerator for a biodegradable resin contains a small amount of the non-biodegradable resin, a content proportion of the non-biodegradable resin is preferably 5 mass % or less, more preferably 3 mass % or less, and even more preferably 1 mass % or less, in 100 mass % total of the biodegradable resin and the non-biodegradable resin.

Because the biodegradation accelerator for a biodegradable resin acts to accelerate the biodegradation of the biodegradable resin, the biodegradation accelerator for a biodegradable resin can be mixed with a biodegradable resin as a molding material and used as a molding material for various applications. In addition, in disposal of an existing biodegradable resin molded product, the biodegradation accelerator for biodegradable resin can be mixed with the existing biodegradable resin molded product.

The biodegradation accelerator for a biodegradable resin can act to accelerate the biodegradation of the biodegradable resin in sea water, fresh water, and soil.

Many biodegradable resins have a low biodegradation speed in sea water even if the biodegradable resins have adequate biodegradability in fresh water or soil. The biodegradation accelerator for a biodegradable resin of an example of the present disclosure is characterized by having the acceleration effect of marine biodegradability.

Biodegradation Acceleration Method for Biodegradable Resin

According to an example, the biodegradation acceleration method for a biodegradable resin is a method including preparing: the biodegradable resin composition containing the biodegradation accelerator for a biodegradable resin and the biodegradable resin; or a molded product thereof, such that a content proportion of the biodegradation accelerator for a biodegradable resin is 0.1 to 80 mass % in terms of the regenerated cellulose in the biodegradable resin composition or the molded product.

In some examples, the biodegradable resin composition or a molded product thereof can be obtained by a method including mixing a blend of a biodegradation accelerator, a biodegradable resin and an optional known additive by a mixer or the like, or a method including melt-kneading the blend by an extruder or the like and molding the melt-kneaded material into a desired form.

In some examples, as the biodegradable resin used in the biodegradable resin composition or a molded product thereof, a biodegradable resin that is the same as the biodegradable resin used in the biodegradation acceleration method for a biodegradable resin can be used.

The content proportion of the biodegradation accelerator for a biodegradable resin in the biodegradable resin composition or a molded product thereof (content proportion in terms of the regenerated cellulose) is preferably from 0.1 to 80 mass %, more preferably from 1 to 60 mass %, even more preferably from 5 to 50 mass %, and yet even more preferably from 10 to 40 mass %.

In the biodegradation acceleration method for a biodegradable resin, the content proportion of the biodegradation accelerator for a biodegradable resin in the biodegradable resin composition or a molded product thereof is adjusted to a predetermined range, and the biodegradation of the biodegradable resin and a molded product thereof can be accelerated in sea water, fresh water, and soil.

Biodegradable Resin Composition

According to one example, the biodegradable resin composition may contain the biodegradation accelerator for a biodegradable resin and a biodegradable resin.

Examples of the biodegradable resin include one or more selected from the group consisting of cellulose ester, starch polyester, polylactic acid (PLA), poly (3-hydroxybutyrate-co-3-hydroxyhexanoate) (PHBH), polylactic acid/polycaprolactone copolymers, polyglycolic acid (PGA), polylactic acid/polyether copolymers, butanediol/long-chain dicarboxylic acid copolymers, polybutylene adipate/terephthalate (PBAT), polytetramethylene adipate-co-terephthalate, polyethylene terephthalate succinate (PETS), polybutylene succinate (PBS), polybutylene succinate adipate (PBSA), and polyvinyl alcohol (PVA).

When the biodegradation accelerator for a biodegradable resin described above contains a biodegradable resin, the biodegradable resin contained in the biodegradable resin composition and the biodegradable resin contained in the biodegradation accelerator may be the same or different.

In some examples, the content proportion of the regenerated cellulose in 100 mass % total of the biodegradable resin in the biodegradable resin composition (including the biodegradable resin contained in the biodegradation accelerator) and the biodegradation accelerator is preferably from 0.1 to 80 mass %, more preferably from 1 to 60 mass %, even more preferably from 5 to 50 mass %, and yet even more preferably from 10 to 40 mass %.

The regenerated cellulose in the biodegradation accelerator acts to accelerate the biodegradation of the biodegradable resin and does not act to improve mechanical strength or physical properties like those described in JP 2016-191021

A, JP 3478299 B, JP 4357859 B, or JP 6551726 B. Thus, even in a case where the content proportion is made small within the range of the content proportion described above, the biodegradation acceleration effect of the biodegradable resin can be exhibited.

Furthermore, in a case where the content proportion is increased within the range of the content proportion, the biodegradation acceleration effect of the biodegradable resin can be further enhanced and, in addition, the regenerated cellulose itself exhibits a reinforcing effect as a filler, and thus a molded product produced from the biodegradable resin composition has an improved mechanical strength and the like. In particular, the use of regenerated cellulose fibers as the regenerated cellulose can enhance the improvement effect in the mechanical strength of a molded product produced from the biodegradable resin composition.

In some examples, the biodegradable resin composition preferably contains no non-biodegradable resin; however, the biodegradable resin composition may contain a small amount of non-biodegradable resin for the reason that, for example, the production facility of the biodegradation accelerator can be shared with a product using a non-biodegradable resin.

In a case where the biodegradable resin composition contains a small amount of the non-biodegradable resin, a content proportion of the non-biodegradable resin is preferably 5 mass % or less, more preferably 3 mass % or less, and even more preferably 1 mass % or less, in 100 mass % total of the biodegradable resin and the non-biodegradable resin.

In some examples, the biodegradable resin composition can contain a known resin additive depending on the application. Examples of such a known resin additive include carbon black, inorganic pigments, organic pigments, dyes, dyeing auxiliaries, dispersing agents, stabilizers, plasticizers, improvers, UV absorbers or light stabilizers, antioxidants, antistatic agents, lubricants, releasing agents, crystallization accelerators, nucleating agents, and elastomers for impact resistance improvement.

When an organic additive is used as the resin additive, an organic additive itself having biodegradability can be used.

In some examples, from the perspective of accelerating biodegradation, the content proportion of such a known resin additive in the biodegradable resin composition is preferably 8 mass % or less, more preferably 3 mass % or less, and even more preferably 1 mass % or less.

However, when the known resin additive is biodegradable, or when the known resin additive is originated from natural material and does not negatively impact the natural environment, the content proportion is not particularly limited.

Biodegradable Resin Molded Product

According to one example, the biodegradable resin molded product is a product produced by forming the biodegradable resin composition described above in a desired form.

In some examples, the biodegradable resin molded product can have various forms such as film-like, sheet-like, plate-like, spherical, hollow bodies, pin-like, stick-like, tube-like, thread-like, rope-like, net-like, and indefinite forms, based on the application.

In some examples, the biodegradable resin molded product can be made into a foam body for the purpose of weight reduction or buoyancy.

In some examples, the biodegradable resin molded product has biodegradability in sea water, fresh water, and soil.

For example, even when the biodegradable resin molded product enters the ocean or reaches the ocean through a river or through lakes or marshes that flows into a river, marine pollution and adverse effect on marine organisms can be prevented or suppressed.

However, the biodegradation is not accelerated in a case where the biodegradable resin molded product is for indoor use or used for machine components that are not exposed to wind and rain. In such a case, with adjustment of the content proportion of the regenerated cellulose (preferably regenerated cellulose fibers), adequate mechanical strength and the like can be imparted.

In some examples, the biodegradable resin molded product is suitable for articles for short-term use or disposable articles, but not for articles for long-term use that requires durability.

However, in some examples, depending on the application, the biodegradation speed can be adjusted for the biodegradable resin molded product. The adjustment can be achieved by exposing the regenerated cellulose on a surface to accelerate the biodegradation or by embedding the regenerated cellulose inside the molded product such that the regenerated cellulose is not exposed on a surface to retard the biodegradation.

As the method for exposing the regenerated cellulose on a surface, a method of polishing the surface by using a file or the like after molding, a method of lowering a mold temperature during injection molding, or the like can be employed. In addition, a method of layering regenerated cellulose films on a surface of the molded product, a method of coating the regenerated cellulose, an in-mold method, or the like can be also employed.

In some examples, the biodegradable resin molded product can be used for an article such as a film, a sheet, a bottle, a tube, woven fabric, nonwoven fabric, various containers (for cosmetics and general goods), a lunch box, a cup, a straw, a spoon, a fork, chopsticks, a toothpick, a plate, a bag, a box, a smartphone case, a glasses frame, a writing implement, household goods, a fishing gear primarily for recreational use, a fishing implement for fishery, and a container for storing marine fishery catches.

As for a container for cosmetics, the biodegradable resin mold product is preferably used for a container of suntan oil or sun block that is often used on the beach.

Examples of the fishing gear for recreational use include a fishing rod, a fishing line, a float, a lure, a hand-held net, and a fishing tackle container. The fishing gear is less frequently used compared to that for professional fishery, and high durability is not particularly required. Meanwhile, because the whole fishing gear or a part of the fishing gear may be discarded in the sea or river, or may enter the sea or river, the present molded product is effective from the perspectives of preventing marine pollution and preventing adverse effect on marine organisms.

Examples of the fishing implement used for fishery and a container for storing marine fishery catches (articles for professional fishery) include a pipe used in aquaculture industry for oysters and the like, a structural plate for an aquaculture float used in the aquaculture industry, a hollow-structure float, a float made of a foam body, an octopus pot, a tubular container for catching eels and congers, and a basket for marine catches such as fish, shellfish, and wakame seaweed.

The article for fishery is always or often in contact with sea water. Even when the article is placed on land or securely fixed in the sea, it is conceived that the article may enter the ocean due to tidal waves, high tides, rainstorms, and the like, or the article may be partially broken and its fragments may enter the ocean. Thus, when the resin material used has high marine biodegradability, its decomposition proceeds during ordinary use, which is not preferred from the perspective of durability.

Thus, in some examples, as the biodegradable resin in the biodegradable resin molded product used for the article for fishery described above, a biodegradable resin having a low marine biodegradation speed is preferably used among the biodegradable resins described above, to achieve durability while maintaining the marine biodegradability. In particular, use of polylactic acid is preferred.

The biodegradable resin molded product containing the regenerated cellulose fibers and the polylactic acid resin has enhanced mechanical strength due to the reinforcing effect of the regenerated cellulose fibers, and has necessary durability during ordinary use. Meanwhile, in a case where the biodegradable resin molded product is damaged after the molded product enters the ocean or a broken part of the product enters the ocean, the regenerated cellulose fibers in the biodegradable resin molded product come into contact with the sea water and this accelerates the decomposition of the polylactic acid resin.

As described above, the biodegradable resin molded product is less likely to decompose during ordinary use, but the decomposition is accelerated when it is damaged. Thus, the biodegradable resin molded product is suitable as an article for fishery.

Treatment Method for Biodegradable Resin Molded Product to be Disposed

According to one example, a treatment method of the biodegradable resin molded product to be disposed is a method of treating a biodegradable resin molded product that has been already in use and that is no longer in need and is ready to be disposed.

In some examples, the treatment method of the biodegradable resin molded product to be disposed is a method including incubating a biodegradable resin molded product to be disposed and the biodegradation accelerator for a biodegradable resin, with the molded product and the biodegradation accelerator being in contact with each other.

To accelerate the biodegradation by increasing a contact area with the biodegradation accelerator for a biodegradable resin, the biodegradable resin molded product to be disposed can be mechanically crushed or mechanically shredded and used. In addition, the biodegradable resin molded product can be made into small debris using a method such as beating and crushing and used.

Examples of the biodegradable resin molded product to be disposed include biodegradable resin molded products made of one or more biodegradable resin(s) selected from the group consisting of cellulose ester, starch polyester, polylactic acid (PLA), poly(3-hydroxybutyrate-co-3-hydroxyhexanoate) (PHBH), polylactic acid/polycaprolactone copolymers, polyglycolic acid (PGA), polylactic acid/polyether copolymers, butanediol/long-chain dicarboxylic acid copolymers, polybutylene adipate/terephthalate (PBAT), polytetramethylene adipate-co-terephthalate, polyethylene terephthalate succinate (PETS), polybutylene succinate (PBS), polybutylene succinate adipate (PBSA), and polyvinyl alcohol (PVA).

In some examples, examples of the method of bringing a biodegradable resin molded product to be disposed and a biodegradation accelerator for a biodegradable resin into contact include a method of mixing the biodegradable resin molded product to be disposed and the biodegradation accelerator for a biodegradable resin to produce a mixture, and a method of wrapping the biodegradable resin molded product to be disposed or the mixture described above with a sheet made of the biodegradation accelerator for a biodegradable resin.

In some examples, the content proportion of the regenerated cellulose in 100 mass % total of the biodegradable resin molded product to be disposed and the biodegradation accelerator is preferably from 0.1 to 80 mass %, more preferably from 1 to 60 mass %, even more preferably from 5 to 50 mass %, and yet even more preferably from 10 to 40 mass %.

Each aspect disclosed in the present specification can be combined with any other feature disclosed herein. Note that the configurations, combinations thereof, and the like in each embodiment of the present disclosure are examples, and various configurational additions, omissions, substitutions, and other changes may be made, as appropriate, without departing from the spirit of the disclosure of the present invention. The present disclosure is not limited by the embodiments and is limited only by the claims.

EXAMPLES

Examples 1 to 5 and Comparative Examples 1 to 4

As each of Examples and Comparative Examples, 30 g total of a sample having components in proportions listed in Table 1 was prepared.

By using Labo Plastomill 4M150, available from Toyo Seiki Seisaku-sho, Ltd., 30 g of each sample was melt-kneaded, and the melt-kneaded material was crushed by a freeze crusher (SPEX Freezer/Mill 6700, available from SPEX).

The crushed material was sieved by using two screen meshes, which were a screen mesh 60 (opening: 250 μm) and a screen mesh 120 (opening: 125 μm), and thus a sample having a particle size of 125 to 250 μm (biodegradable resin composition) was obtained.

The used components were as described below.

PCL: Polycaprolactone, PLACCEL HIP [available from Daicel Corporation]

3-Hydroxybutyrate-co-3-hydroxyhexanoate (PHBH): Straw for Seven Cafe made of Kaneka biodegradable polymer PHBH was used.

EC210: Cellulose acetate-based resin (available from Daicel Miraizu Ltd.)

Polylactic acid (PLA): LUMINY L-105 (available from Total Corbion PLA)

Regenerated cellulose fibers 1: Material obtained by cutting CR500, number of filament: 2700 (Viscose rayon, available from Cordenka GmbH & Co. KG) into a length of 5 mm.

Regenerated cellulose fibers 2: TENCEL (fibers obtained by spinning using N-methylmorpholine-N-oxide as a solvent) FCP (available from Lenzing) (fiber length: 0.6 mm)

Marine Biodegradability Test

In a testing equipment 1 (volume: 0.5 L, BOD Tester 10 D, available from Taitec Corporation) illustrated in FIG. 1, containing 0.1 L of sea water (sampled in July 2020 from the sea in front of Hirohata Plant of Daicel Miraizu Ltd. in Himeji-shi, Hyogo Prefecture), approximately 10 mg of each sample was placed. Each sample was completely soaked in the sea water (liquid phase) 2. In this state, the sample was maintained at 25° C.±1° C. for 64 days, and the degree of biodegradability was determined on 35th day and 64th day.

The degree of biodegradation was evaluated by the amount of oxygen consumption (Amg). The amount of oxygen consumption was determined based on pressure change in the container, after carbon dioxide was absorbed by the absorbent, where the carbon dioxide had been generated by the biodegradation of the resin sample by microorganisms. Furthermore, as a blank, the amount of oxygen consumption (A1 mg) in a testing equipment containing no sample but only the sea water was measured and evaluated. A greater amount of oxygen consumption indicates better degree of biodegradation. The degree of biodegradation was calculated based on the following equation.

$$\text{Degree of biodegradation } (\%) = (A - A1)/(B \times 10) \times 100$$

B: Amount of oxygen consumption (mg) required to decompose all the resin sample placed in the testing equipment, and this value is a theoretical value calculated based on the molecular structure.

TABLE 1

| | Example 1 | Comparative Example 1 | Example 2 | Comparative Example 2 | Example 3 | Comparative Example 3 | Example 4 | Comparative Example 4 | Example 5 |
|---|---|---|---|---|---|---|---|---|---|
| PCL | 95 | 100 | | | | | | | |
| PHBH | | | 95 | 100 | | | | | |
| EC210 | | | | | 95 | 100 | | | 95 |
| PLA | | | | | | | 95 | 100 | |
| Regenerated cellulose fibers 1 | 5 | | 5 | | 5 | | 5 | | |
| Regenerated cellulose fibers 2 | | | | | | | | | 5 |
| Total (mass %) | 100 | 100 | 100 | 100 | 100 | 100 | 100 | 100 | 100 |
| Kneading temperature (° C.) | 120 | — | 210 | — | 210 | — | 210 | — | 210 |
| Kneading time (min) | 5 | — | 3 | — | 3 | — | 3 | — | 3 |
| Degree of biodegradation | 39 | 28 | 59 | 51 | 20 | 19 | 4 | 2 | — |

TABLE 1-continued

| | Example 1 | Comparative Example 1 | Example 2 | Comparative Example 2 | Example 3 | Comparative Example 3 | Example 4 | Comparative Example 4 | Example 5 |
|---|---|---|---|---|---|---|---|---|---|
| on 35th day (%) Degree of biodegradation on 64th day (%) | — | — | — | — | 47 | 37 | 11 | 5 | 48 |

As is clear from the results in Table 1, by using the biodegradation accelerator for a biodegradable resin (regenerated cellulose fibers), the biodegradability of the biodegradable resin was accelerated. Note that the degree of biodegradation at 64th day of cellulose, which was a reference, was 75%.

Examples 6 to 8 and Comparative Example 5

A fiber bundle made of long rayon fibers (CR500, number of filament: 2700) was passed through a crosshead die. At this time, to the crosshead die, a component (A) listed in Example 6 of Table 2 in a molten state was supplied from a twin-screw extruder (cylinder temperature: 230° C.), and the molten material was impregnated into the rayon fiber bundle.

Next, the material was shaped with a shaping nozzle at the outlet of the crosshead die, and the shape was further refined with a shape refining roll, after which the sample was cut to a predetermined length (7 mm) using a pelletizer to obtain a pellet-like (cylindrical) resin-impregnated long fiber bundle (biodegradable resin composition).

When the resin-impregnated long fiber bundle obtained in this manner was cut and inspected, in Example 6, the rayon fibers were almost aligned parallel to the length direction, and the resin had impregnated into the center of the fiber bundle.

Production of a test piece (biodegradable resin molded product) was performed by injection molding in the following conditions.

Pellet drying condition: 100° C., 4 hours
Cylinder temperature: 210° C.

Mold temperature: 40° C.

In Example 6, a test piece (biodegradable resin molded product) was obtained by injection-molding the resin-impregnated long fiber bundle (biodegradable resin composition) produced in Example 6. In each of Examples 7 and 8, the resin-impregnated long fiber bundle (biodegradable resin composition) produced in Example 6 and PLA pellets were dry-blended in a ratio listed in Table 2 and dried, and then injection-molded, and thus each test piece (biodegradable resin molded product) was obtained.

Using the obtained test piece (biodegradable resin molded product), each evaluation test listed in Table 2 was performed. Note that marine biodegradability test was performed in the same manner as in Examples 1 to 5 by using 0.1 L of sea water (sampled in July 2021 from the sea in front of Hirohata Plant of Daicel Miraizu Ltd. in Himeji-shi, Hyogo Prefecture).

The used components were as described below.

PLA: Luminy 130 (available from Total Corbion PLA)

Regenerated cellulose fibers 3: CR500, number of filament: 2700 (Viscose rayon, available from Cordenka GmbH & Co. KG)

PLA-RF40: Composite material (material produced in Example 6) of 60 mass % of PLA (Luminy 130) and 40 mass % of regenerated cellulose fibers

TABLE 2

| | | | | Examples | | | Comparative Examples |
|---|---|---|---|---|---|---|---|
| | | | | 6 | 7 | 8 | 5 |
| Composition | PLA | | | 60 | 62.5 | 87.5 | 100 |
| | Regenerated cellulose fibers 3 | | | 40 | | | |
| | PLA-RF40 | | | | 37.5 | 12.5 | |
| | Total (mass %) | | | 100 | 100 | 100 | 100 |
| | Regenerated cellulose fiber content (mass %) | | | 40 | 15 | 5 | 0 |
| Evaluation test | Tensile strength | MPa | ISO527 | 120 | 97 | 72 | 77 |
| | Flexural Strength | MPa | ISO178 | 205 | 150 | 120 | 100 |
| | Flexural modulus | MPa | ISO178 | 8700 | 5500 | 4200 | 3500 |
| | Charpy Impact Strength | kJ/m² | ISO179/1eA | 42 | 8.5 | 4.5 | 1.8 |
| | Temperature of deflection under load | ° C. | ISO75 | 76 | 61 | 57 | 52 |
| | Density | g/cm³ | ISO1183 | 1.3 | 1.26 | 1.24 | 1.24 |
| | Degree of biodegradation on 35th day | % | | — | 9 | — | 0 |
| | Degree of biodegradation on 64th day | % | | — | 13 | — | 0 |

As is clear from Table 2, for the biodegradable resin composition according to an embodiment of the present invention and the molded product obtained by the biodegradable resin composition, mechanical properties can be adjusted by adjusting the content of the regenerated cellulose fibers.

From the comparison between Table 1 and Table 2, it was confirmed that appropriate mechanical strength can be imparted depending on the application while the biodegradability in the sea and the like can be maintained. The degree of biodegradation at 64th day of cellulose, which was a reference, was 63%.

Note that, although Comparative Example 4 in Table 1 and Comparative Example 5 in Table 2 used the same PLA, there were differences between the degrees of biodegradation on 35th day and on 64th day. It is conceived that this is because the amount and type of microorganisms contained in the sea water were different due to the difference in the sampled years of the sea water samples.

INDUSTRIAL APPLICABILITY

Because the biodegradation accelerator for a biodegradable resin of an example of the present disclosure can act to accelerate the biodegradability of a biodegradable resin, the biodegradation accelerator can be blended in various products containing biodegradable resins and can be used to accelerate the biodegradability of a biodegradable resin product to be disposed.

REFERENCE SIGNS LIST

1 Testing equipment
2 Liquid phase (sea water phase)
3 Gas phase (air phase)
4 $CO_2$ absorbent

The invention claimed is:

1. A biodegradable resin composition comprising a biodegradation accelerator for a biodegradable resin and a biodegradable resin,
    the biodegradation accelerator comprising a regenerated cellulose, wherein
    the regenerated cellulose is selected from the group consisting of fibers, molded products including films, powders, cotton-like objects, and intermediate molded bodies,
    a biodegradation speed for a biodegradable resin is accelerated compared to a case where the biodegradation accelerator for a biodegradable resin is not used, and
    a content proportion of the biodegradation accelerator for a biodegradable resin is from 0.1 to 50 mass % in terms of a regenerated cellulose in the biodegradable resin composition.

2. The biodegradable resin composition according to claim 1, wherein a content proportion of the biodegradation accelerator for a biodegradable resin is from 0.1 to 40 mass % in terms of a regenerated cellulose in the biodegradable resin composition.

3. The biodegradable resin composition according to claim 1, wherein the biodegradable resin is selected from the group consisting of cellulose ester, starch polyester, polylactic acid (PLA), poly(3-hydroxybutyrate-co-3-hydroxyhexanoate) (PHBH), polylactic acid/polycaprolactone copolymers, polyglycolic acid (PGA), polylactic acid/polyether copolymers, butanediol/long-chain dicarboxylic acid copolymers, polybutylene adipate/terephthalate (PBAT), polytetramethylene adipate-co-terephthalate, polyethylene terephthalate succinate (PETS), polybutylene succinate (PBS), polybutylene succinate adipate (PBSA), and polyvinyl alcohol (PVA).

4. The biodegradable resin composition according to claim 1, wherein the biodegradable resin is a cellulose ester selected from the group consisting of cellulose acetate, cellulose propionate, cellulose butyrate, cellulose acetate propionate, cellulose acetate butyrate, polycaprolactone grafted cellulose acetate, acetyl methyl cellulose, acetyl ethyl cellulose, acetyl propyl cellulose, acetyl hydroxyethyl cellulose, and acetyl hydroxypropyl cellulose.

5. A biodegradable resin molded product comprising the biodegradable resin composition according to claim 1.

6. The biodegradable resin molded product according to claim 5, wherein the biodegradable resin molded product has biodegradability in sea water, fresh water, and soil.

7. The biodegradable resin molded product according to claim 5, wherein the biodegradable resin molded product is an article including a fishing implement used in fishery and a container for containing caught marine products.

8. The biodegradable resin molded product according to claim 7, wherein the biodegradable resin is polylactic acid.

9. A method for treating the biodegradable resin molded product according to claim 5, the method comprising incubating the biodegradable resin molded product, with the biodegradable resin and the biodegradation accelerator being in contact with each other.

10. The method for treating the biodegradable resin molded product according to claim 9, wherein the biodegradable resin molded product is mechanically crushed or mechanically shredded.

11. The method for treating the biodegradable resin molded product according to claim 9, wherein the biodegradable resin molded product contains the biodegradable resin selected from the group consisting of cellulose ester, starch polyester, polylactic acid (PLA), poly(3-hydroxybutyrate-co-3-hydroxyhexanoate) (PHBH), polylactic acid/polycaprolactone copolymers, polyglycolic acid (PGA), polylactic acid/polyether copolymers, butanediol/long-chain dicarboxylic acid copolymers, polybutylene adipate/terephthalate (PBAT), polytetramethylene adipate-co-terephthalate, polyethylene terephthalate succinate (PETS), polybutylene succinate (PBS), polybutylene succinate adipate (PBSA), and polyvinyl alcohol (PVA).

* * * * *